United States Patent [19]
Kawula et al.

[11] Patent Number: 5,397,305
[45] Date of Patent: Mar. 14, 1995

[54] FIXED-WIRE DILATATION CATHETER WITH ROTATABLE BALLOON ASSEMBLY

[75] Inventors: Paul J. Kawula, Sunnyvale; Ray R. Beitelia, San Jose; Erik J. vander Burg, Mountain View; Michael S. Williams, Cupertino, all of Calif.

[73] Assignee: Advanced Cardiovascular Systems, Inc., Santa Clara, Calif.

[21] Appl. No.: 983,602

[22] Filed: Nov. 30, 1992

Related U.S. Application Data

[63] Continuation of Ser. No. 631,657, Dec. 21, 1990, abandoned.

[51] Int. Cl.$^6$ .............................. A61M 29/00
[52] U.S. Cl. .................... 604/96; 606/194; 604/103
[58] Field of Search ................ 604/95–99, 604/103, 126; 606/191, 192, 194, 195

[56] References Cited

U.S. PATENT DOCUMENTS

| | | |
|---|---|---|
| 3,629,018 | 9/1972 | Goetz et al. |
| 3,939,820 | 2/1976 | Grayzel |
| 3,978,863 | 9/1976 | Fettel et al. |
| 4,338,942 | 7/1982 | Fogarty |
| 4,456,000 | 6/1984 | Schjeldahl et al. |
| 4,531,937 | 7/1985 | Yates ........................ 604/53 |
| 4,582,181 | 4/1986 | Samson |
| 4,638,805 | 1/1987 | Powell ...................... 606/192 |
| 4,771,778 | 9/1988 | Mar ........................... 604/96 |
| 4,793,350 | 12/1988 | Mar et al. |
| 4,813,934 | 3/1989 | Engelson et al. ......... 604/99 |
| 4,917,088 | 4/1990 | Crittenden |
| 4,976,720 | 12/1990 | Machold et al. .......... 606/194 |
| 4,981,478 | 1/1991 | Evard et al. ............... 604/282 |
| 4,998,917 | 3/1991 | Gaiser et al. .............. 604/96 |
| 4,998,923 | 3/1991 | Samson et al. ........... 606/194 |
| 5,024,658 | 6/1991 | Kozlov et al. ............. 604/101 |
| 5,055,109 | 10/1991 | Gould et al. ............... 604/95 |
| 5,120,308 | 6/1992 | Hess ........................... 604/96 |
| 5,135,487 | 8/1992 | Morrill et al. |

FOREIGN PATENT DOCUMENTS

| | | |
|---|---|---|
| 0347023 | 12/1989 | European Pat. Off. |
| 0368523 | 5/1990 | European Pat. Off. |
| 0376132 | 7/1990 | European Pat. Off. |
| 2078114 | 6/1981 | United Kingdom |
| 8901352 | 2/1989 | WIPO |

*Primary Examiner*—C. Fred Rosenbaum
*Assistant Examiner*—Ronald K. Stright, Jr.
*Attorney, Agent, or Firm*—Fulwider Patton Lee & Utecht

[57] ABSTRACT

A fixed-wire dilatation catheter for angioplasty procedures which has an inflated balloon on the distal end with little or no tendency to wrap on itself when the catheter is advanced through a patient's vascular system. The catheter comprises an elongated torquable shaft which is longitudinally relatively flexible but diametrically relatively rigid, a guide extension secured to the distal end of the elongated torquable shaft, and a balloon assembly which is mounted about the distal section of the torquable shaft and the guide member so that the balloon assembly is free to rotate about the torquable shaft and guide member and thereby avoid balloon wrapping. An elongated flexible member such as a helical coil is secured to the portion of the guide member which extends distally of the balloon.

40 Claims, 2 Drawing Sheets

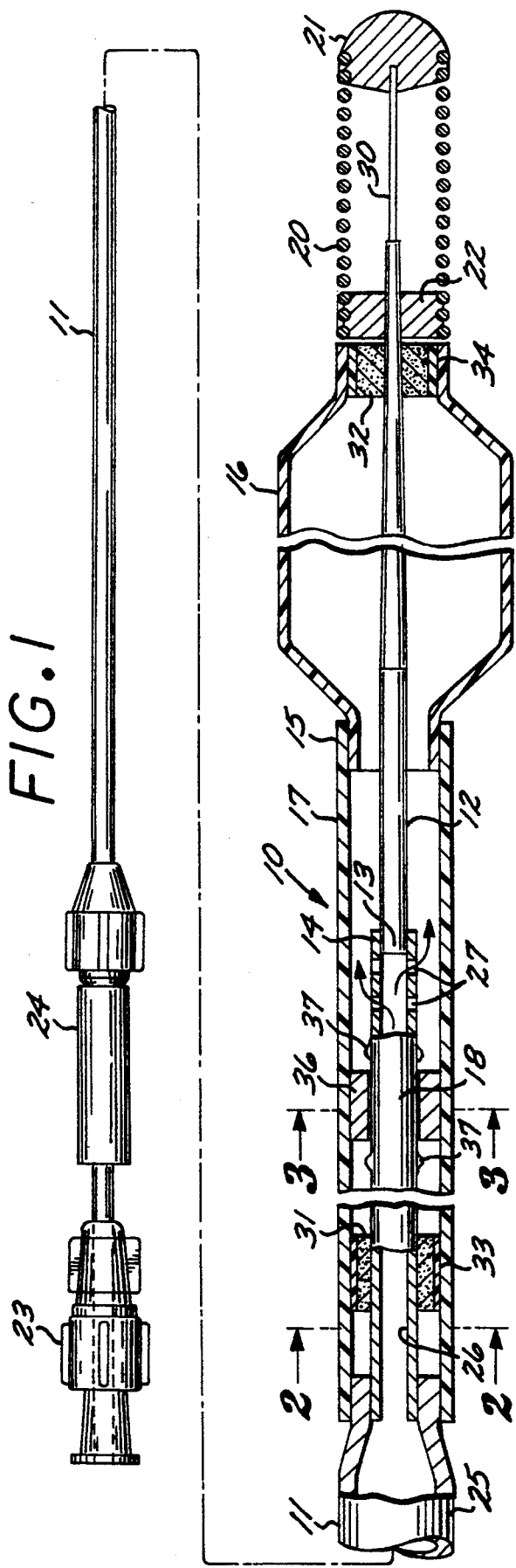
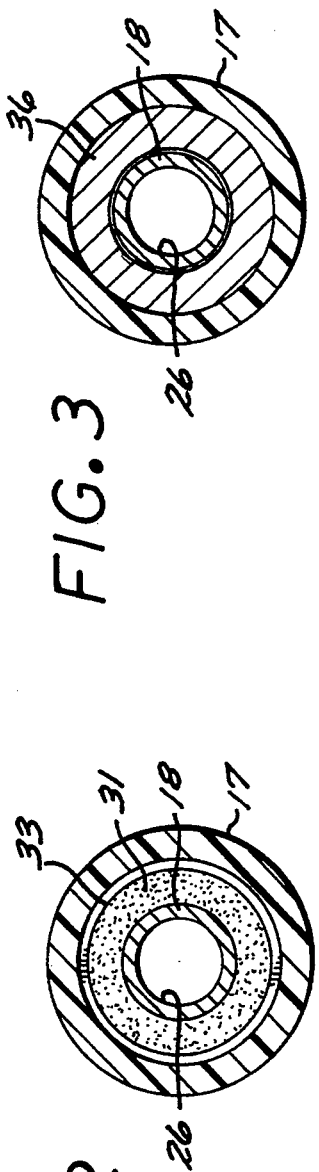

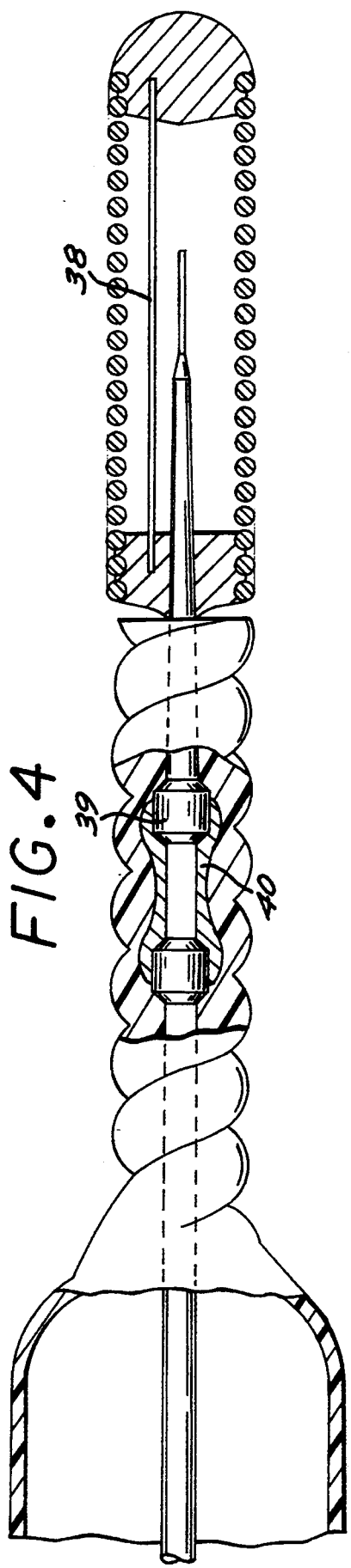
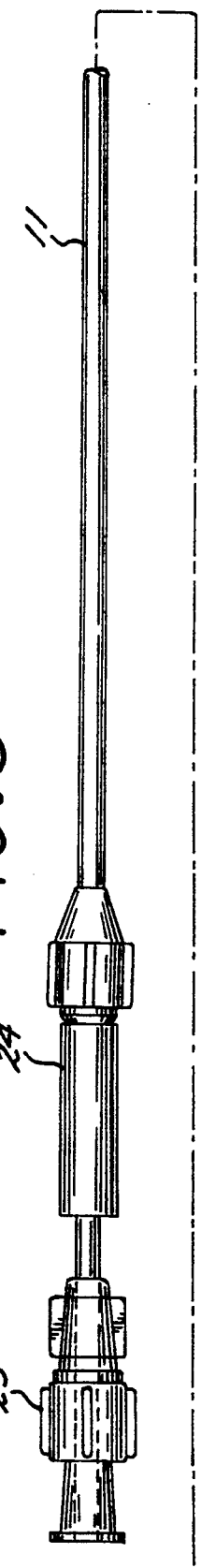
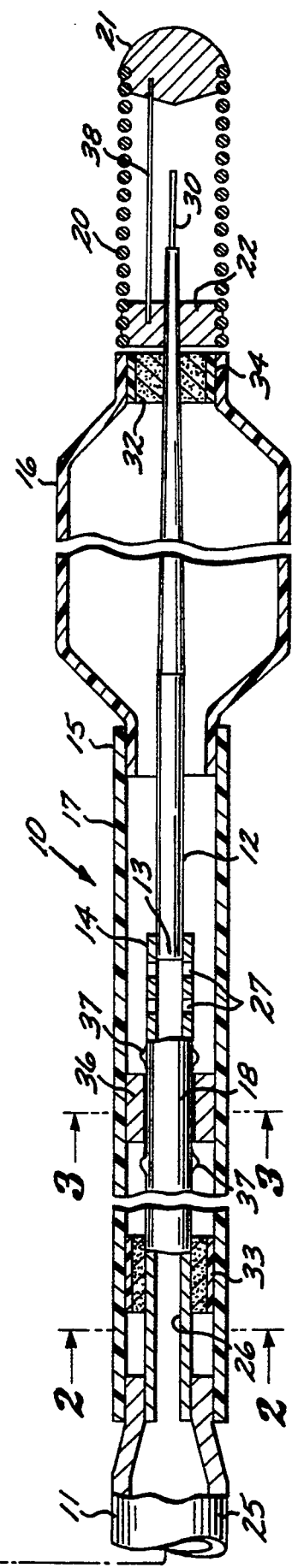
FIG. 4  FIG. 5

FIXED-WIRE DILATATION CATHETER WITH ROTATABLE BALLOON ASSEMBLY

This is a continuation of application(s) Ser. No. 07/631,657, filed on Dec. 21, 1990, now abandoned.

BACKGROUND OF THE INVENTION

This invention generally relates to fixed-wire balloon dilatation catheters for angioplasty procedures, such as percutaneous transluminal coronary angioplasty (PTCA), and particularly to fixed-wire catheters which have little or no propensity for balloon wrapping while being advanced through a patient's vascular system.

In classic PTCA procedures, a guiding catheter having a preshaped distal tip is percutaneously introduced into the cardiovascular system of a patient and advanced therein until the preshaped distal tip thereof is disposed within the aorta adjacent the ostium of the desired coronary artery. The guiding catheter is twisted or torqued from the proximal end to turn the distal tip of the guiding catheter so that it can be guided into the coronary ostium. A dilatation catheter having a balloon on the distal end thereof and a guidewire slidably disposed within an inner lumen thereof is introduced into and advanced through the guiding catheter to its distal tip. The guidewire is first advanced out the distal tip of the guiding catheter, which is seated in the ostium of the patient's coronary artery, until the distal end of the guidewire crosses the lesion to be dilated. The dilation catheter is then advanced out of the distal tip of the guiding catheter, over the previously advanced guidewire, until the balloon on the distal extremity of the dilatation catheter is properly positioned across the lesion. Once properly positioned, the balloon is inflated to a predetermined size with radiopaque liquid at relatively high pressures (e.g., generally 4–12 atmospheres) to dilate the stenosed region of the diseased artery. The balloon is then deflated so that the dilatation catheter can be removed from the dilated stenosis and blood flow resumed therethrough.

Further details of guiding catheters, dilatation catheters, guidewires, and the like for angioplasty procedures can be found in U.S. Pat. No. 4,323,071 (Simpson-Robert); U.S. Pat. No. 4,439,185 (Lundquist); U.S. Pat. No. 4,468,224 (Enzmann et al.); U.S. Pat. No. 4,516,972 (Samson); U.S. Pat. No. 4,438,622 (Samson et al.); U.S. Pat. No. 4,554,929 Samson et al.); U.S. Pat. No. 4,582,181 (Samson); U.S. Pat. No. 4,616,652 (Simpson); U.S. Pat. No. 4,638,805 (Powell); U.S. Pat. No. 4,748,986 (Morrison et al.) and U.S. Pat. No. 4,898,577 (Badger et al.) which are hereby incorporated herein in their entirety by reference thereto.

Fixed-wire dilatation catheters with built-in guidewires or guiding elements are frequently used because the deflated profile of such catheters are generally smaller than conventional dilatation catheters having the same inflated balloon size and these catheters have greater pushability due to the guidewire being fixed therein. Further details of fixed-wire dilatation catheters may be found in U.S. Pat. Re. No. 33,166 (Samson), U.S. Pat. No. 4,619,263 (Frisbie et al.), U.S. Pat. No. 4,641,654 (Samson et al.), U.S. Pat. No. 4,664,113 (Frisbie et al.), U.S. Pat. No. 4,771,778 (Mar) and U.S. Pat. No. 4,793,350 (Mar et al.) which are hereby incorporated in their entirety by reference thereto. The lower profile of these catheters allows them to cross tighter lesions and to be advanced much deeper into a patient's coronary anatomy.

However, it has been found that the inflatable balloons of commercially available fixed-wire dilatation catheters tend to wrap on themselves as they are advanced through a patient's vascular system, particularly when torqued from the proximal end. As a result of the wrapping, the balloon frequently may not inflate completely or, if inflated, may not deflate within a desired time period. Some suppliers of such fixed-wire catheters have recommended that their catheters be limited to one rotation to avoid balloon wrapping. However, such restrictions on rotations severely limit the steerability of the catheter within a patient's vasculature.

What has been needed and heretofore unavailable is a fixed-wire dilatation catheter having a very low profile which can be torqued from the proximal end thereof without wrapping the inflatable balloon thereon. The present invention satisfies this and other needs.

SUMMARY OF THE INVENTION

This invention is directed to a fixed-wire dilatation catheter having a distal end construction which prevents the inflatable balloon thereof from wrapping upon itself as it is advanced through a patient's vasculature.

The fixed-wire dilatation catheter of the invention generally comprises an elongated torquable shaft having an inner lumen extending along the length thereof, an elongated guide member secured by the proximal end thereof to the distal end of the torquable shaft and a balloon assembly disposed about the distal portion of the torquable shaft and a proximal portion of the guide member. The balloon assembly is mounted so that it is free to rotate with respect to the torquable shaft with the attached guide member. As the fixed-wire catheter is advanced through a patient's arterial system, the torquable shaft and attached guide member freely rotate within the balloon assembly so there is little or no chance for the balloon to wrap.

The elongated torquable shaft includes a main tubular section, a more flexible distal section, an inner lumen extending along the length thereof, and at least one inflation port in the distal section thereof which is in fluid communication with the inner lumen. The torquable shaft is relatively flexible in the longitudinal direction but diametrically relatively rigid, and it does not expand to any significant degree under internal pressures experienced in angioplasty procedures. The more flexible distal section may have a smaller outer diameter than the main tubular section to provide increased flexibility.

The guide member has proximal and distal ends and is preferably tapered toward its distal end. It is secured by suitable means such as welding at its proximal end to the distal end of the main tubular section of the torquable shaft.

An elongated flexible member, such as a helical coil or a cylindrical plastic member (e.g., polyethylene or polyurethane), having a rounded distal end is coaxially disposed about the portion of the guide member which extends distally of the balloon. The flexible member is joined by suitable means to the guide member at one or more locations along the length thereof.

The structure of the catheter tip distally of the balloon can be of standard design wherein the distal tip of the guide member is secured to the rounded plug at the distal tip of the coil. Alternatively, the distal tip structure may have a floppy design wherein the distal tip of the coil extends beyond the distal tip of the guide member and a shaping ribbon extends from an intermediate location to the rounded plug in the distal tip of the coil where it is secured.

The balloon assembly includes an inflatable balloon with a tubular extension on the proximal end thereof. The distal end of the balloon and the proximal end of the tubular extension are sealed about the torquable shaft and the guide member which extends therethrough to prevent the escape of inflation liquid, but the assembly is mounted to allow the torquable shaft with the attached guide member and the balloon assembly to be freely rotatable with respect to each other so as to prevent balloon wrapping. The distal section of the torquable shaft has one or more inflation ports to direct inflation fluid from the inner lumen extending within the torquable shaft to the interior of the balloon. The seal of the tubular extension of the balloon assembly about the torquable shaft is proximal to the inflation ports therein to ensure that these ports are in fluid communication with the interior of the inflatable balloon. The distal end of the balloon is likewise sealingly secured about the portion of the guide member extending therethrough to prevent the escape of inflation fluid and yet allow relative rotation between the distal end of the balloon and the portion of the torquable shaft and guide member passing therethrough. The tubular extension of the balloon assembly should be radially relatively rigid and longitudinally relatively flexible, but it should be more flexible than the distal section of the torquable shaft. The balloon should be made from flexible but relatively inelastic materials.

The proximal end of the elongated torquable shaft has an adapter with means to introduce inflation liquid into the inner lumen of the torquable shaft and it also has means to apply torque thereto for the purpose of steering the catheter through patient's vascular system.

In a presently preferred embodiment, the elongated tubular shaft is a hypotube formed of stainless steel (e.g. type 304) or other suitable materials, such as Nitinol (a nickel-titanium alloy) having superelastic properties which are described in copending application Ser. No. 07/629,381 filed Dec. 18, 1990. The use of hypotubing allows the dilatation catheter to be made with profiles as low as 0.010 inch (0.254 mm). Even though the hypotube may be formed of high-strength materials and is diametrically rather rigid, the diameter-to-length ratio is sufficiently low that the elongated tubular member made therefrom is still relatively flexible. The hypotube provides excellent pushability.

In accordance with a preferred embodiment of the invention, both ends of the balloon assembly are freely rotatable about the portions of the torquable shaft and guide member extending therethrough, so the balloon is unable to wrap upon itself when the catheter is torqued from the proximal end during the advancement of the catheter through the patient's arteries.

These and other advantages of the fixed-wire dilatation catheter of the invention will become more apparent from the following detailed discussion thereof, when taken in conjunction with the accompanying exemplary drawings.

BRIEF DESCRIPTION OF THE DRAWINGS

FIG. 1 is an elevational view, partially in section, of a steerable fixed-wire dilatation catheter embodying features of the invention;

FIG. 2 is a transverse cross-sectional view taken along the lines 2—2 shown in FIG. 1;

FIG. 3 is a transverse cross-sectional view taken along the lines 3—3 shown in FIG. 1;

FIG. 4 is an elevational view partially in section of an alternative embodiment of the invention; and FIG. 5 is an elevational view, partially in section, of an alternative embodiment of the invention.

DETAILED DESCRIPTION OF THE INVENTION

FIG. 1 illustrates a fixed-wire dilatation catheter assembly 10 embodying features of the invention. As shown, the catheter assembly 10 generally includes an elongated torquable shaft 11, a guide member 12 joined at the proximal end 13 thereof to the distal end 14 of the torquable shaft 11 and a balloon assembly 15 which comprises a balloon 16 and a tubular extension 17 and which is mounted about the distal section 18 of the torquable shaft 11 so that it is freely rotatable about the torquable shaft and the guide member 12.

A flexible coil 20 having a rounded plug 21 on the distal end thereof is disposed about and secured to the portion of the guide member 12 which extends out the distal end of the balloon 16 at a suitable location 22 distally of the balloon 16.

A removable hub 23, such as the Luer lock shown, is connected to the proximal end of the elongated torquable shaft 11 to facilitate connection to a source for radiopaque inflation fluid. The torquing knob 24 on the proximal end of the torquable shaft 11 permits the torquing of the catheter when it is advanced through a patient's vasculature.

The elongated torquable shaft 11 is preferably hypotubing formed from stainless steel, such as type 304 stainless steel, or other suitable materials such as Nitinol which has been thermomechanically processed to have superelastic properties. The shaft 11 has a main tubular section 25 and a smaller diameter, more flexible distal section 18 and has an inner lumen 26 extending through both tubular sections. The distal tubular section 18 has one or more inflation ports 27 therein to direct inflation fluid from the inner lumen 26 into the interior of the balloon 16 for the inflation thereof. Inflation fluid is introduced into the inner lumen 26 at the proximal end of the torquable shaft through hub 23.

Typical dimensions of the torquable shaft 11 include an overall length of about 135 to about 145 cm. The main section 25 has an outside diameter of about 0.018 inch (0.457 mm), an inside diameter of about 0.012 inch (0.305 mm) and a length of about 90 to about 120 cm. The small diameter distal section 18 has an outside diameter of about 0.012 inch (0.305 mm), an inner diameter of about 0.008 inch (0.203 mm) and a length of about 10 to about 15 cm. The distal section 18 is seated within the distal end of the main tubular section 25 and secured therein by suitable adhesive such as Loctite 405. The torquable member 11 is provided with sequentially smaller diameters toward the distal end thereof to increase the flexibility thereof. These smaller diameter sections can be formed by joining sections of tubing having sequentially smaller diameters, as shown in the FIG. 1 or by drawing the tubular sections of the torquable member 11 with sequentially smaller outer diameters. The inflation ports 27 in the smaller diameter distal section 18 have a diameter of about 0.003 inch (0.076 mm) and are formed with a MS35 YAG laser.

The proximal end of the guide member 12 is suitably secured about 3 to 4 mm within the distal end of the main tubular section 25 by welding. The guide member 12 is about 25 to about 40 cm in length and tapers in the distal direction to smaller diameters to provide greater flexibility to the distal end of the catheter assembly 10. In the presently preferred embodiment, the first taper is about 5–7 mm long and reduces the outer diameter from about 0.007 to about 0.006 inch (0.176–0.152 mm) and the second taper is about 2.0 to 2.5 cm long and has a reduction in diameter of from 0.006 to about 0.0025 inch (0.152–0.064 mm). The most distal portion 30 of guide member 12 is preferably flattened to a rectangular transverse cross section of about 0.001 by 0.003 inch (0.025–0.076 mm) to provide even greater flexibility in a single plane and also to facilitate the manual shaping thereof which is necessary to be able to steer the catheter through the patient's arteries. The guide member 12 may be in the form of a solid rod or a hollow tube.

The coil 20 is secured to the guide member 12 at location 22 by suitable means such as brazing or soldering. The wire from which the coil 20 is formed is about 0.0025 inch (0.063 mm) in diameter and is preferably formed of a palladium-platinum-molybdenum alloy. The plug 21 generally is formed by welding the distal tip of the guide member 12 to the distal end of the coil 20 and is rounded to minimize arterial damage as the catheter is advanced through a patient's vascular system.

In the balloon assembly 15 the proximal end of the balloon 16 is adhesively secured to the distal end of the tubular extension 17. The proximal end of tubular extension 17 extends over the distal end of the small diameter distal section 18 proximally beyond the inflation ports 27. An annular sealing member 31, which is preferably secured by a suitable adhesive to the inside of the tubular extension 17, is disposed about the small diameter distal section 18 proximal to the inflation ports 27. A similar annular sealing member 32, which is also preferably secured by a suitable adhesive to the inside of the distal end of the balloon 16, is disposed about the portion of the guide member 12 which extends therethrough. These sealing members preferably contain hydrophilic materials which swell upon contact with the aqueous based inflation fluid so as to seal the proximal and distal ends of the balloon assembly 15 to prevent the loss of inflation fluid during balloon inflation. Suitable materials, which are described more completely in co-pending application Ser. No. 547,469, filed Jul. 2, 1990, including polyacrylamides such as Hypan sold by Kingston Technology of Dayton, N.J. and high molecular weight (e.g. 5,000,000) polyethylene oxide such as POLY-OX sold by Union Carbide Corporation. The hydrophilic materials are in the form of powder which is compacted within small diameter, heat shrinkable tubular sections 33 and 34 disposed at the desired locations along the guide member 12. The heat shrinkable tubular members 33 and 34 are then subjected to elevated temperatures, e.g. 285° F. for high density polyethylene, to heat shrink the tubular sections and the compacted hydrophilic material therein about the guide member 12.

Air readily passes through a bed of the powdered hydrophilic material so that any air trapped within the interior of the balloon 16 will be driven through the sealing bed when the balloon is inflated with the aqueous based inflation fluid but, as soon as the aqueous-based inflation fluid contacts the hydrophilic material, it swells, thereby blocking off the further passage of the aqueous-based liquid.

A bearing 36 is rotatably mounted on the distal tubular section 18 between the raised projections or stops 37 which restrict the relative axial movement of the bearing. The outer diameter of the bearing 36 is secured to the inside of the tubular extension 17 by means of an adhesive such as Loctite FMD-13.

An alternate embodiment having a distal construction commonly identified as a floppy design, is shown in FIG. 4. In this embodiment the distal end of the guide element 12 does not extend to the distal end of the coil 21, but instead it is joined to the coil 20 at an intermediate location. A shaping ribbon 38 extends from the brazement at location 22 to the plug 21. The ribbon, 38 is manually bent or curved to facilitate the steering of the distal end of the catheter into a desired blood vessel during angioplasty procedures. In a presently preferred embodiment, the shaping ribbon 38 is formed of material stronger than the material of the guide member 12 such as tungsten or tungsten alloys and it has typical transverse cross-sectional dimensions of about 0.001×0.003 inch (0.025×0.076 mm).

In the alternate embodiment shown in FIG. 4, the distal end of the balloon 16 is secured to the guidewire member 12 by twisting the distal end and heat shrinking the twisted end as described in co-pending application Ser. No. 521,103, filed May 9, 1990, which is incorporated herein by reference. In this embodiment, bearings 39, preferably stainless steel, are fixed to the shaft of the guide member 12 and are disposed within a sealing coating 40 of hydrophilic powdered material which swells upon contact with the aqueous inflation fluid, but which allows the passage of air therethrough prior to the contact with the aqueous based liquid. A suitable lubricant (e.g., silicon lubricant) may be provided between the heat shrunk distal end and the guide member 12 to prevent any adhesion between them and to facilitate the relative rotation therebetween.

The materials of construction for the fixed-wire catheter of the invention may be conventional materials. The use of hypotubing for the torquable shaft have already been described. The balloon 16 should be made of flexible and relatively inelastic material and is preferably formed of biaxially oriented polyethylene, polyethylene terephthalate, nylon polyimide, polyvinyl chloride or polyurethane. The polyethylene terephthalate balloon is blown from tubing having an intrinsic viscosity of less than 1.0. The tubular extension 17 of the balloon assembly 15 is preferably thin-walled polyimide tubing which is described in co-pending application Ser. No. 220,563, filed Jul. 18, 1988, which is hereby incorporated herein by reference. The polyimide tubing is longitudinally more flexible than and radially not quite as rigid as hypotubing, but it will not expand significantly upon inflation of the balloon 16 during angioplasty procedures. The balloon assembly 15 preferably has a lubricious coating of polysiloxane bonded to the external surface thereof to help in advancing the catheter through arteries and also to prevent wrapping. A particularly suitable siloxane coating is described in co-pending application Ser. No. 559,373, filed Jul. 24, 1990, which is hereby incorporated herein by reference. A preferred composition for the shaping ribbon 38 of the alternative embodiment shown in FIG.4 is a tungsten-rhenium alloy as described in co-pending application Ser. No. 534,345, filed May 16, 1990, which is incorporated herein by reference. The bearing 36 may be metallic or plastic in nature. It should be apparent to those skilled in the art that other materials as well as other structures can be employed in the fixed-wire catheters of the invention. For example, the balloon assembly 15 can be formed of the same plastic material in a unitary construction rather than joining by a suitable adhesive such as Loctite FMD-13 the distal end of tubular extension 17 to the proximal end of balloon 16 of different compositions.

To the extent not previously mentioned, typical dimensions of the steerable, fixed-wire dilatation catheter of the invention include an overall length of up to 150 cm or higher, a tip coil length from about 1 to 3 cm, a balloon length of about 1 to 3 cm, and inflated balloon diameters from about 1 to about 5 mm. Deflated profiles for the balloon range from about 0.01 to about 0.025 inch (0.254 mm–0.635 mm), preferably less than about 0.02 inch (0.508 mm), so that the dilatation catheter can be inserted through an inner lumen of a standard dilatation catheter.

The low-profile, steerable, fixed-wire dilatation catheter of the invention can be used in the same manner as prior low-profile steerable dilatation catheters. It can be readily advanced through very tortuous arterial passageways with essentially no risk of wrapping the balloon on itself, thus ensuring complete inflation and deflation when it is positioned within a stenosis to be dilated. The Luer lock 23 connection on the proximal end of the torquable member 11 in accordance with the invention provides the further advantage that the Luer connection can be removed, an exchange wire inserted into the proximal end of the torquable member and a standard dilatation catheter can be advanced over the fixed-wire catheter of the invention. Other uses of the invention will become apparent to those skilled in the art.

While the above description of the invention is directed to presently preferred embodiments, various modifications and improvements can be made without departing from the scope of the invention.

What is claimed is:

1. An intravascular catheter, comprising:
   a) an elongated catheter body with an inner lumen extending therein;
   b) an expandable member freely rotatably mounted to the catheter body near its distal extremity;
   c) means for setting the interior of said expandable member in fluid communication with the inner lumen of the catheter body;
   d) a guide element supported within the catheter which extends through at least part of the interior of the expandable member and out the distal end thereof;
   e) means for preventing the loss of fluid from within the expandable member's interior; and
   f) means for preventing longitudinal movement of the guide element relative the catheter.

2. The intravascular catheter of claim 1 including means disposed between the distal end of the expandable member and the portion of the guide element extending therethrough to allow the passage of gas but preclude the passage of liquid therethrough.

3. The intravascular catheter of claim 2 wherein the means to allow the passage of gas but preclude the passage of liquid therethrough is a hydrophilic material disposed between the distal end of the expandable member and the guide element which expands sufficiently upon contact with an aqueous based liquid to prevent the passage therethrough of liquid under relatively high pressure.

4. The intravascular catheter of claim 3 wherein the hydrophilic material which expands upon contact with aqueous based liquid is in porous form.

5. The intravascular catheter of claim 3 wherein the hydrophilic material is selected from the group consisting of polyacrylamide or high molecular weight polyethylene.

6. The intravascular catheter of claim 1 comprising means to prevent relative longitudinal movement between the guide element and the distal end of the expandable member.

7. The intravascular catheter of claim 6 wherein the means to prevent relative longitudinal movement between the guide element and the distal end of the expandable member include at least two radially extending protrusions longitudinally spaced along the exterior of the guide element and an annular bearing affixed to said expandable member which is rotatably mounted about the guide element between two of the radially extending protrusions.

8. An intravascular catheter, comprising:
   a) an elongated catheter body with an inner lumen extending therein;
   b) an expandable member freely rotatably mounted to the catheter body near its distal extremity so as to prevent relative longitudinal movement;
   c) means for setting the interior of said expandable member in fluid communication with the inner lumen of the catheter body;
   d) a guide element supported within the catheter which extends through at least part of the interior of the expandable member and out the distal end thereof;
   e) bearing means to support the distal end of the expandable member about the guide element so as to prevent relative longitudinal movement while allowing free relative rotation therebetween; and
   f) means for preventing the loss of fluid from within the expandable member's interior out its distal end.

9. The fixed-wire dilatation catheter, comprising:
   a) an elongated torquable shaft;
      which has a main tubular section and a more flexible, relatively short distal tubular section distal to the main tubular section;
      which has an inner lumen extending through the main and distal tubular sections; and
      which has at least one inflation port in the distal tubular section in fluid communication with the inner lumen;
   b) a guide member;
      which has proximal and distal ends; and
      which is secured by the proximal end thereof to the distal tubular section of the torquable shaft;
   c) an inflatable assembly disposed about said torquable shaft so as to be freely rotatable relative thereto, and longitudinally fixed relative thereto;
      which has proximal and distal ends;
      which has an inflatable member with an interior in fluid communication with the inflation port; and
      which has a proximal tubular extension disposed about at least a portion of the distal tubular section of the torquable shaft and at least a portion of the guide element which is in fluid communication with said inflatable member and said inflation port to thereby define an inflation lumen;

d) means to allow free relative rotational movement between the inflatable member assembly and the torquable shaft; and
e) means for sealing the inflatable assembly about said torquable shaft to prevent loss of inflation fluid from the inflatable assembly upon the inflation of the inflatable member.

10. A fixed-wire dilatation catheter, comprising:
a) an elongated torquable shaft which includes a main tubular section and a relatively more flexible distal tubular section;
   an inner lumen extending through the main and distal tubular sections; and
   at least one inflation port in the distal tubular section which sets said tubular section's exterior into fluid communication with the inner lumen;
b) a guide member which has proximal and distal ends, and which is secured by its proximal end to the distal tubular section of the torquable shaft; and
c) a balloon assembly which includes:
   a tubular extension having a proximal end and a distal end, and which is disposed about at least a portion of the distal tubular section of the torquable shaft and at least a portion of the guide member such that the interior of said tubular extension is in fluid communication with said inner lumen via said inflation port;
   means for rotatably attaching the proximal end of said tubular extension to said elongated torquable shaft so as to allow free rotation therebetween;
   means for sealing between said tubular extension and said torquable shaft allowing free rotation therebetween
   an inflatable balloon, having a proximal end and a distal end, and which is disposed about said guide member, its proximal end being affixed to said tubular extension and in fluid communication therewith;
   means for rotatably attaching the distal end of said balloon to said guide member so as to allow free rotation therebetween; and
   means for sealing between the distal end of said balloon and said guide member allowing free rotation therebetween whereby the balloon assembly is freely rotatable about the torquable shaft and guide member.

11. The fixed-wire dilatation catheter of claim 10 wherein the means for rotatably attaching the tubular extension to said elongated shaft includes an annular bearing which is secured to the inside of the tubular extension of the balloon assembly and is rotatably disposed about the distal tubular section.

12. The fixed-wire dilatation catheter of claim 11 further comprising means to prevent relative longitudinal movement between the annular bearing and the distal tubular section of the torquable shaft.

13. The fixed-wire dilatation catheter of claim 12 wherein the longitudinal movement preventing means include radially extending protrusions longitudinally spaced along the exterior of the distal tubular section of the torquable shaft.

14. The fixed-wire dilatation catheter of claim 13 wherein said annular bearing is rotatably mounted about the distal tubular section between said radially extending protrusions that are longitudinally spaced along the exterior of the distal tubular section of the torquable shaft.

15. The fixed-wire dilatation catheter of claim 10 wherein a portion of said guide member extends out the distal end of the balloon assembly and wherein a flexible body is disposed about and secured thereto.

16. The fixed dilatation catheter of claim 15 wherein said flexible body has a distal end and wherein a rounded plug is formed in said distal end.

17. The fixed-wire dilatation catheter of claim 16 wherein a shaping ribbon having proximal and distal ends is secured at the proximal end thereof to the guide member and at the distal end thereof to the rounded plug.

18. The fixed-wire dilatation catheter of claim 17 wherein the shaping ribbon is formed of a metal selected from the group consisting of tungsten, rhenium, and alloys thereof and stainless steel.

19. The fixed-wire dilatation catheter of claim 15 wherein the flexible body is a helical coil.

20. The fixed-wire dilatation catheter of claim 19 wherein a distal portion of the coil is formed of radiopaque material.

21. The fixed-wire dilatation catheter of claim 15 wherein the flexible body is a helical coil or an elongated body of flexible plastic.

22. The fixed-wire dilatation catheter of claim 16 wherein the distal end of the guide member is secured to the rounded plug.

23. The fixed-wire dilatation catheter of claim 16 wherein the distal end of the guide member terminates short of the rounded plug.

24. The fixed-wire dilatation catheter of claim 15 wherein said flexible body has a distal end and wherein the distal end of the guide member is secured to the flexible body at an intermediate location proximal to the distal end thereof.

25. The fixed-wire dilatation catheter of claim 10 including means to vent air from the interior of the balloon displaced during the inflation of the balloon with inflating liquid.

26. The fixed-wire dilatation catheter of claim 25 wherein the venting means includes hydrophilic material disposed between the distal end of the balloon and the guide member which expands sufficiently upon contact with an aqueous based liquid to prevent the passage therethrough of liquid under relatively high pressure.

27. The fixed-wire dilatation catheter of claim 26 wherein the hydrophilic material is formed of polyacrylamide or high molecular weight polyethylene.

28. The fixed-wire dilatation catheter of claim 26 wherein the tubular extension is formed of polyimide.

29. The fixed-wire dilatation catheter of claim 10 wherein the means for sealingly between the distal end of the balloon and the guide member prevents the loss of fluid but allows the passage of air therethrough.

30. The fixed-wire dilatation catheter of claim 29 wherein the means for sealingly attaching the distal end of the balloon and the guide member include a porous body which swells upon contact with an aqueous liquid.

31. The fixed-wire dilatation catheter of claim 29 wherein the means for sealing between the distal end of the balloon and the guide member extending therethrough is secured to the inside of the distal end of the balloon.

32. The fixed-wire dilatation catheter of claim 10 wherein the main tubular section of the torquable member is formed of metal and is relatively flexible with respect to lateral loads but relatively rigid with respect to torque loads.

33. The fixed-wire dilatation catheter of claim 32 wherein the metal is selected from the group consisting of stainless steel and a nickel-titanium alloy having superelastic properties.

34. The fixed-wire dilatation catheter of claim 10 wherein the outer diameter of the main tubular section is less than 0.02 inch.

35. The fixed-wire dilatation catheter of claim 10 wherein the balloon is formed from a plastic material selected from the group consisting of polyethylene, polyethylene terephthalate, nylon, polyimide, polyvinyl chloride and polyurethane.

36. The fixed-wire dilatation catheter of claim 10 wherein torque means is secured to the main tubular section at or near the proximal end thereof.

37. The fixed-wire dilatation catheter of claim 10 wherein a removable hub is secured to the proximal end of the main tubular section.

38. The fixed-wire dilatation catheter of claim 10 wherein the guide member extends through the interior of the balloon and the distal end of the balloon is sealed about the distal end of the guide member.

39. The fixed-wire dilatation catheter of claim 10 wherein the tubular extension has a wall thickness of less than 0.002 inch.

40. The fixed-wire dilatation catheter of claim 10 wherein said balloon is formed from a tube of polyethylene terephthalate material having an intrinsic viscosity of less than 1.

* * * * *

UNITED STATES PATENT AND TRADEMARK OFFICE
CERTIFICATE OF CORRECTION

PATENT NO. : 5,397,305
DATED : March 14, 1995
INVENTOR(S) : Paul J. Kawula, Ray R. Beitelia, Erik J. vander Burg and Michael S. Williams It is certified that error appears in the above-indentified patent and that said Letters Patent is hereby corrected as shown below:

Column 10, line 58, change "for sealingly attaching" to --for sealingly between--.

Signed and Sealed this

Thirteenth Day of February, 1996

Attest:

BRUCE LEHMAN

Attesting Officer

Commissioner of Patents and Trademarks